US011041966B2

(12) United States Patent
Chappo

(10) Patent No.: US 11,041,966 B2
(45) Date of Patent: Jun. 22, 2021

(54) RADIATION DETECTOR SCINTILLATOR WITH AN INTEGRAL THROUGH-HOLE INTERCONNECT

(71) Applicant: KONINKLIJKE PHILIPS N.V., Eindhoven (NL)

(72) Inventor: Marc Anthony Chappo, Elyria, OH (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 16/339,057

(22) PCT Filed: Oct. 18, 2017

(86) PCT No.: PCT/EP2017/076550
§ 371 (c)(1),
(2) Date: Apr. 3, 2019

(87) PCT Pub. No.: WO2018/077681
PCT Pub. Date: May 3, 2018

(65) Prior Publication Data
US 2020/0041667 A1 Feb. 6, 2020

Related U.S. Application Data

(60) Provisional application No. 62/412,876, filed on Oct. 26, 2016.

(51) Int. Cl.
*G01T 1/20* (2006.01)
*G01T 1/208* (2006.01)
(Continued)

(52) U.S. Cl.
CPC .......... *G01T 1/2018* (2013.01); *A61B 6/4241* (2013.01); *A61B 6/482* (2013.01);
(Continued)

(58) Field of Classification Search
CPC ....... G01T 1/2018; G01T 1/208; G01T 1/161; G01T 1/202; G01T 1/242; G01T 1/2008; A61B 6/4241; A61B 6/482
See application file for complete search history.

(56) References Cited

U.S. PATENT DOCUMENTS

| 4,234,792 A | 11/1980 | Decou | |
|---|---|---|---|
| 6,285,740 B1 * | 9/2001 | Seely | ...................... H05G 1/20 250/367 |

(Continued)

FOREIGN PATENT DOCUMENTS

| JP | 2010216893 | 9/2010 |
|---|---|---|
| WO | 2016/046216 | 3/2016 |
| WO | 2017025888 | 2/2017 |

*Primary Examiner* — Kiho Kim
(74) *Attorney, Agent, or Firm* — Larry Liberchuk

(57) ABSTRACT

A scintillator layer (206) includes a plurality of scintillator pixels (337), walls of non-scintillation material (336) surrounding each of the plurality of scintillator pixels, and at least one electrically conductive interconnect (224) for a pixel, wherein the at least one electrically conductive interconnect extends within a wall of the pixel along an entire depth of the wall. A multi-energy detector array (114) includes a detector tile (116) with an upper scintillator layer (202), an upper photosensor (204) optically coupled to the upper scintillator layer, a lower scintillator layer (206) electrically coupled to the upper photosensor, and a lower photodetector (208) optically and electrically coupled to the lower scintillator layer. The lower scintillator layer includes at least one scintillator pixel (337) surrounded by at least one wall of non-scintillation material (336), and the wall includes at least one electrically conductive interconnect (224) that extends from a top edge of the wall to a bottom edge of the wall.

25 Claims, 4 Drawing Sheets

(51) Int. Cl.
 *G01T 1/161* (2006.01)
 *A61B 6/00* (2006.01)
 *G01T 1/24* (2006.01)

(52) U.S. Cl.
 CPC .............. *G01T 1/161* (2013.01); *G01T 1/208* (2013.01); *G01T 1/2008* (2013.01); *G01T 1/242* (2013.01)

(56) References Cited

U.S. PATENT DOCUMENTS

| | | |
|---|---|---|
| 6,921,909 B2 | 7/2005 | Nagarkar |
| 7,569,832 B2 * | 8/2009 | Tredwell ............... G01T 1/2018 250/370.11 |
| 7,612,342 B1 | 11/2009 | Nagarkar |
| 9,000,382 B2 * | 4/2015 | Mattson ............... G01T 1/2018 250/363.01 |
| 9,012,857 B2 | 4/2015 | Levene |
| 2006/0151708 A1 * | 7/2006 | Bani-Hashemi ...... G01T 1/2018 250/370.11 |
| 2008/0011960 A1 * | 1/2008 | Yorkston ................. G21K 4/00 250/370.09 |
| 2008/0023637 A1 * | 1/2008 | Heismann ............. G01T 1/2018 250/366 |
| 2008/0315106 A1 | 12/2008 | Buchinsky |
| 2009/0129538 A1 * | 5/2009 | Tkaczyk ................ A61B 6/032 378/5 |
| 2013/0292574 A1 | 11/2013 | Levene |
| 2015/0276939 A1 | 10/2015 | Chappo |

* cited by examiner

RADIATION DETECTOR SCINTILLATOR WITH AN INTEGRAL THROUGH-HOLE INTERCONNECT

CROSS REFERENCE TO RELATED APPLICATIONS

This application is the U.S. National Phase application under 35 U.S.C. § 371 of International Application No. PCT/EP2017/076550, filed Oct. 18, 2017 published as WO 2018/077681 on May 3, 2018, which claims the benefit of U.S. Provisional Patent Application No. 62/412,876 filed Oct. 26, 2016. These applications are hereby incorporated by reference herein.

FIELD OF THE INVENTION

The following generally relates to a scintillator for a radiation detector and more particularly to a scintillator array with at least one through-hole interconnect in at least one wall of at least one scintillator pixel of the scintillator array, and is described herein with particular application to computed tomography (CT), but is also amenable to other imaging modalities.

BACKGROUND OF THE INVENTION

A computed tomography (CT) radiation detector includes crystal or garnet scintillators directly mounted to solid-state photodetectors such as photodiodes. The scintillator material produces light photons in response to absorbing X-ray photons, and the light photons are converted to electrical signals by the photodetector. The electrical signals are processed to generate an image. A multi-layer spectral (multi-energy) CT detector includes either vertically arranged detectors or horizontally arranged detectors. Both types of detectors include at least two (dual energy) stacked scintillators, one above the other, with one closer to the radiation source and the other further away from the radiation source, and each tuned to a different photon energy range.

With vertically arranged detectors, the photodetectors are mounted to sides of the scintillators. With horizontally arranged detectors, at least photodetector is mounted between scintillators. As such, horizontally arranged detectors require flex or other circuitry to route signals from a photodetector that is between scintillators, around the lower of the scintillators, and to the processing electronics for image generation. Unfortunately, such flex or other circuitry is in the path of the X-ray beam and attenuates X-ray photons, which reduces dose efficiency in that some X-rays traversing a patient are attenuated by the flex or other circuitry and not detected, and thus irradiate the patient but do not contribute to the final image.

SUMMARY OF THE INVENTION

Aspects described herein address the above-referenced problems and/or others.

In one aspect, a scintillator layer includes a plurality of scintillator pixels, walls of non-scintillation material surrounding each of the plurality of scintillator pixels, and at least one electrically conductive interconnect (224) for a pixel, wherein the at least one electrically conductive interconnect extends within a wall of the pixel along an entire depth of the wall.

In another aspect, a multi-energy detector array includes a stacked detector tile including: an upper scintillator layer, an upper photosensor optically coupled to the upper scintillator layer, a lower scintillator layer electrically coupled to the upper photosensor, and a lower photodetector optically and electrically coupled to the lower scintillator layer. The lower scintillator layer includes at least one scintillator pixel surrounded by at least one wall of non-scintillation material, and the at least one wall includes at least one electrically conductive interconnect that extends from a top edge of the wall at the upper photosensor to a bottom edge of the wall at the lower photodetector.

In another aspect, a method for routing photosensor signals in a stacked multi-energy detector tile including at least an upper scintillator layer, an upper photosensor optically coupled to the upper scintillator layer, a lower scintillator layer electrically coupled to the upper photosensor, and a lower photodetector optically and electrically coupled to the lower scintillator layer, includes: receiving, at the upper scintillator layer, X-ray photons including first energy X-ray photons and second energy X-ray photons, wherein the first energy is less than the second energy, converting, with the upper scintillator layer, the first energy X-ray photons to first light photons, detecting, with the upper photosensor, the first light photons and producing a first electrical signal indicative thereof, routing, through a through-hole interconnects in a side wall of the lower scintillator layer, the first electrical signal to the lower photodetector, and routing, with the lower photodetector, the first electrical signal to processing electronics.

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
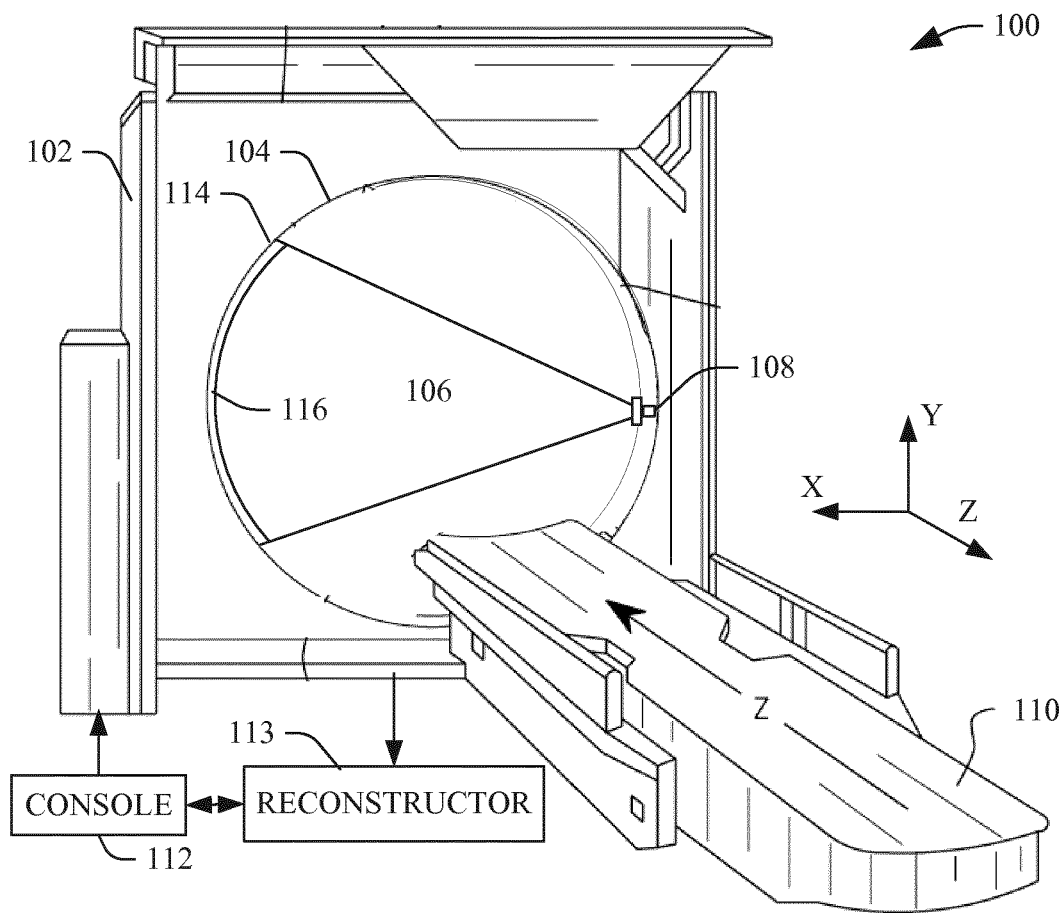
FIG. 1 diagrammatically illustrates an example imaging system with a detector module with a detector tile that includes a scintillator layer with an integral through-hole interconnect.

FIG. 1 diagrammatically illustrates an imaging system 100 such as a computed tomography (CT) scanner. The imaging system 100 includes a generally stationary gantry 102 and a rotating gantry 104. The rotating gantry 104 is rotatably supported by the stationary gantry 102 by a bearing (not visible) or the like and rotates around an examination region 106 about a longitudinal or z-axis. A radiation source 108, such as an X-ray tube, is supported by and rotates with the rotating gantry 104, and emits X-ray radiation that traverse the examination region 106. A subject support 110, such as a couch, supports a subject or object in the examination region 106. A computer serves as an operator console 112 and includes human readable output devices such as a display and input devices such as a keyboard and/or mouse. Software resident on the console 112 allows the operator to control an operation of the imaging system 100, and view images generated by a reconstructor 113.

Figure 2:
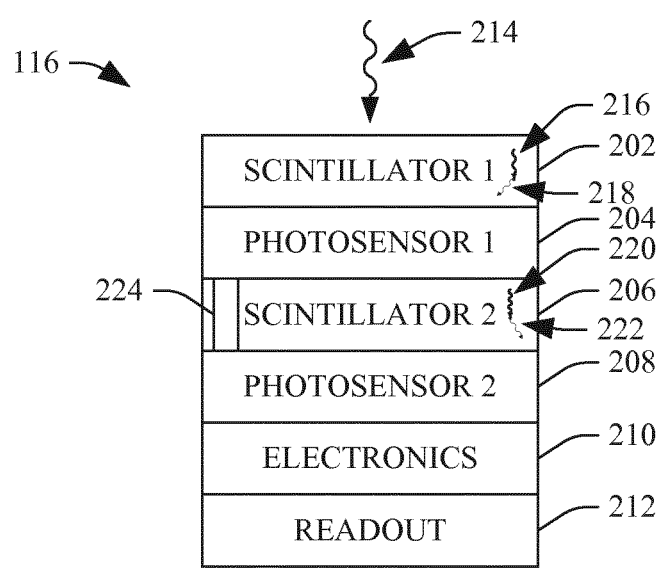
FIG. 2 diagrammatically illustrates an example of the detector tile, including the scintillator layer with the integral through-hole interconnect.

A multi-energy (spectral) radiation sensitive detector array 114 subtends an angular arc opposite the radiation source 108 across the examination region 106, detects radiation traversing the examination region 106, and generates and outputs an electrical signal indicative thereof. The multi-energy radiation sensitive array 114 includes a plurality of detector tiles 116, each with a plurality of scintillation layer/photosensor layer pairs, one for each different energy. FIG. 2 shows a non-limiting example of the detector tile 116 configured for dual energy. However, tiles 116 for more than two energies are also contemplated herein. The detector tile 116 includes a plurality of horizontally stacked layers, including a first (upper) scintillator layer 202, a first (upper) photosensor layer 204 optically coupled thereto, a second (lower) scintillator layer 206 electrically coupled thereto, a second (lower) photosensor layer 208 optically and electrically coupled thereto, processing electronics (e.g., an application specific integrated circuit, or ASIC) 210 electrically coupled thereto, and readout electronics 212 electrically coupled thereto. The relative geometry (i.e., shape, size, etc.) of the detector tile 116 and the components therein is not limiting. An example of a dual layer horizontally stacked detector is described in U.S. Pat. No. 9,012,857 B2, filed May 7, 2012, and entitled "Multi-layer Horizontal Computed Tomography (CT) Detector Array with at least one Thing Photosensor Array Layer Disposed Between at least Two Scintillator Array Layers," the entirety of which is incorporated herein by reference.

Each tile 116 is spatially oriented in the system 100 such that the first scintillator layer 202 is closest to the source 108 and X-ray photons 214 emitted by the source 108. Lower energy X-ray photons 216 are absorbed by the first scintillation layer 202, which converts these X-ray photons into light photons 218. Higher energy X-ray photons 220 pass through the first scintillation layer 202 and are absorbed by the second scintillation layer 206, which converts these X-ray photons into light photons 222. Generally, absorption by the first and second scintillator layers 202 and 206 is dependent on a thickness of a scintillation material and/or a type of the scintillator material(s). Examples of suitable materials include scintillation nanomaterials, quantum dots, etc., gadolinium oxy sulfide ("GOS"), zinc selenide (ZnSe), cadmium tungstate (CdWO$_4$) or other scintillation material. An example of a detector with one or more quantum dot scintillator layers is described in patent application Ser. No. 62/202,397, filed Aug. 7, 2015, and entitled "Quantum Dot Based Imaging Detector," the entirety of which is incorporated herein by reference. An example of a quantum dot is described in application serial number EP 14186022.1, entitled "Encapsulated materials in porous particles," and filed on Sep. 23, 2014, the entirety of which is incorporated herein by reference.

The first photosensor layer 204 detects the light photons 218 produced by the first scintillation layer 202 and generates an electrical signal indicative thereof. As described in greater detail below, this electrical signal is routed through at least one through-hole interconnect 224 (e.g., an integral vertical interconnect access (VIA)) in at least one wall surrounding a scintillator pixel of the second scintillator layer 206 and through the second photosensor layer 206 to the processing electronics 210. As a result, the detector tile 116 does not require flex or other circuitry disposed above the second scintillator layer 206 to bypass the second scintillator layer 206 and route the electrical signals from the first photosensor layer 204 to the processing electronics 210. As such, dose efficiency is improved, complexity and assembly cost are reduced, and reliability is increased, relative to a configuration in which flex or other circuitry is mounted between the first photosensor layer 204 and the second scintillator layer 206. The second photosensor layer 208 detects the light photons 222 produced by the second scintillation layer 206 and generates an electrical signal indicative thereof. This electrical signal is routed directly to the processing electronics 210, and is sent to the reconstructor 113 via the readout electronics 212.

Returning to FIG. 1, a reconstructor 113 reconstructs the signals output by the array 114 and generates volumetric three-dimensional image data. In one instance, for a dual energy configuration, this includes reconstructing lower energy image data with the signal from the first photosensor layer 204 and/or reconstructing higher energy image data with the signals from the second photosensor layer 208. The image data can be combined to approximate image data from a non-spectral scanner. Additionally or alternatively, the signal from the first photosensor layer 204 and the signal from the second photosensor layer 208 are first combined, and then then reconstructor 113 reconstructs image data similar to conventional, non-spectral image data from a non-spectral scanner. Additionally or alternatively, the reconstructor 113 reconstructs both the lower and higher energy image data and the single image similar to the non-spectral scanner. Generally, image data can be generated for each energy level in a multi-energy configuration and/or a combination of the energy levels.

Figure 3:
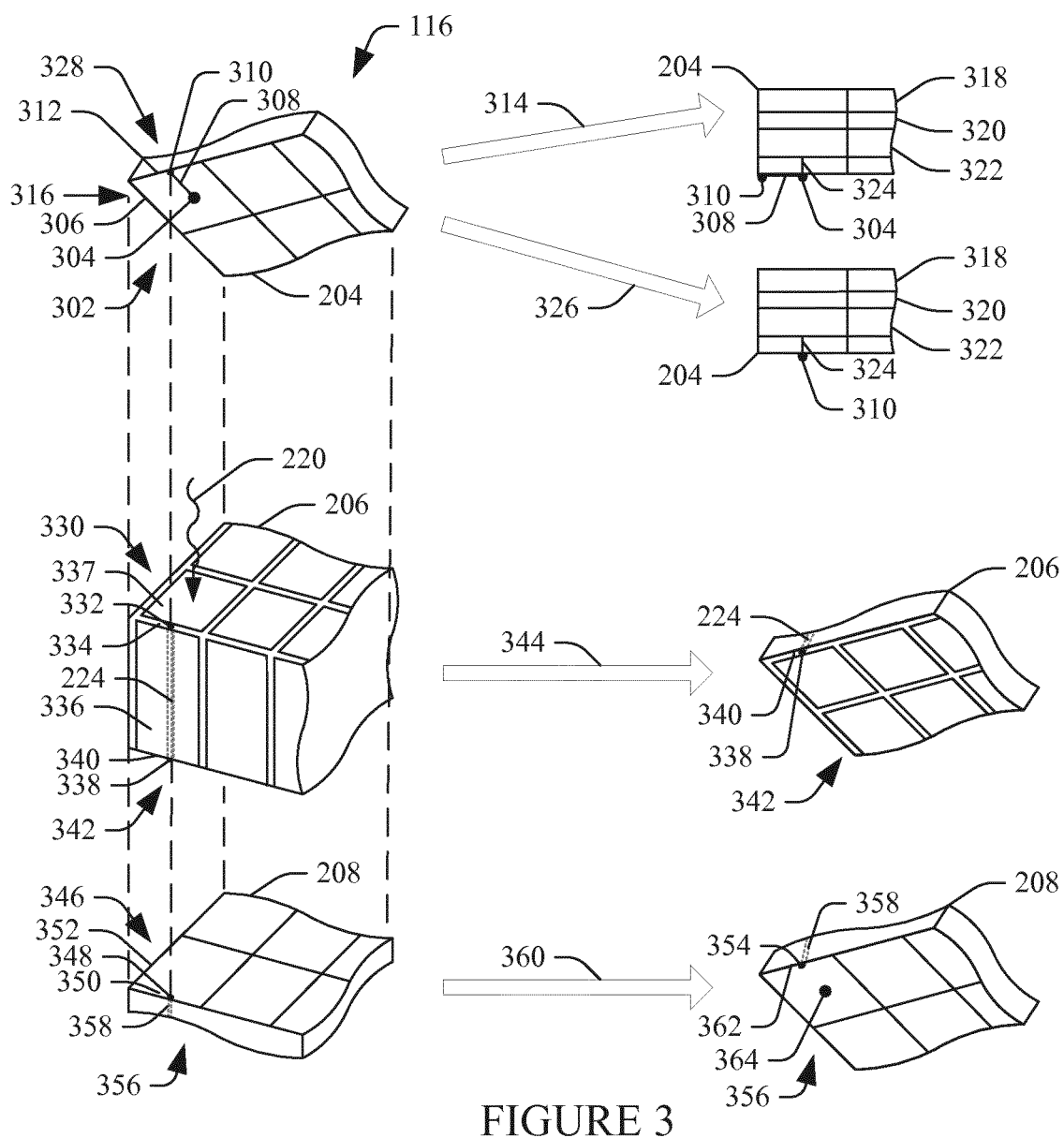
FIG. 3 diagrammatically illustrates an exploded view of a sub-portion of the detector tile, including the scintillator layer with the integral through-hole interconnect and upper and lower photosensors with corresponding electrical interconnects.

Turning to FIG. 3, an exploded view of the detector tile 116, showing the first photosensor layer 204, the second scintillator layer 206 with the integral through-hole interconnect 224, and the second photosensor layer 208, is diagrammatically illustrated. For clarity and brevity, the following describes the integral through-hole interconnect 224 in connection with a single wall of a single pixel of the tile 116. However, it is to be understood that the other walls, including multiple walls, and/or other pixels of the tile 116 are likewise configured.

The exploded view shows a perspective view of the first photosensor layer 204 from a bottom 302 of the first photosensor layer 204. A readout electrode 304 of a photosensor pixel 306 is disposed on the bottom 302. The electrical signal indicative of the light collected by the photosensor pixel 306 is routed off the photosensor pixel 306 from the readout electrode 304. The illustrated readout electrode 304 is located at a center region of the photosensor pixel 306. In a variation, the electrode 304 is located off-center or outside of the center region of the photosensor pixel 306. An electrical trace 308 extends along the bottom 302 from the readout electrode 304 to an electrical contact 310 at an edge 312 of the photosensor pixel 306.

Figure 4:
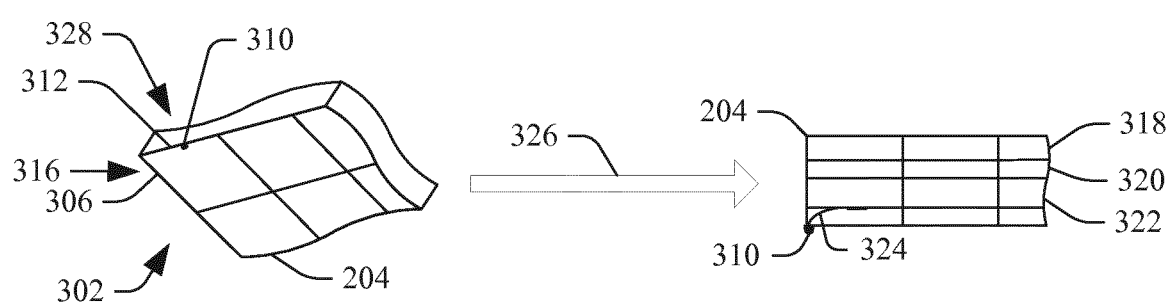
FIG. 4 diagrammatically illustrates a variation of a photosensor interconnect described in FIG. 3.

At 314, a view from a side 316 of the photosensor pixel 306 is shown. In the illustrated embodiment, the photosensor pixel 306 includes a PIN diode with a positive (p-) type region 318, an intrinsic region 320, and a negative (n-) type region 322. The n-type region 322 is in electrical contact with the readout electrode 304 through an electrically conductive member 324. At 326, a view from a side 328 of the photosensor pixel 306 is shown. Generally, the sides 316 and 328 are perpendicular for square or rectangular pixels. FIG. 4 shows a variation in which the electrically conductive member 324 extends, inside of the first photosensor layer 204, directly from the n-type region 322 to the electrical contact 310 at the edge 312 of the photosensor pixel 306, and the electrode 304 and the electrical trace 308 are omitted.

Returning to FIG. 3, the exploded view also shows a perspective view from a top 330 of the second scintillator layer 206. In this example, the through-hole interconnect 224 extends from a top contact 332 at a top edge 334 of a wall 336 adjacent to a scintillator pixel 337, within the wall 336, to a bottom contact 338 at a bottom edge 340 of the wall 336 at a bottom 342 of the second scintillator layer 206. In general, the wall 336 (and other walls surrounding each scintillator pixel) includes non-scintillation material and a light reflective material (e.g., coating, film, paint, etc.), which reflects light towards the bottom 342 and hence the second photosensor layer 208, improving collection efficiency and reducing cross-talk. The contact 310 of the first photosensor layer 204 and the top contact 332 of the second scintillator layer 206 are in physical and electrical contact in the assembled structure. At 344, a perspective view from the bottom 342 of the second scintillator layer 206 is illustrated, showing the through-hole interconnect 224 and the contact 338 at the bottom edge 340 of the second scintillation layer 206.

In general, the second scintillator layer 206 is made of the same material(s) used in conventional CT scintillators and in the same manner except an electrically conductive material (an electrically conductive metal, electrically conductive nanomaterials, quantum dots (e.g., silicon), etc.) is constructed into one or more side walls of one or more scintillation pixels. For example, the second scintillator layer 206 can be a printed, molded, sintered, etc. structure, with the through-hole interconnect 224 formed in the wall 336. In another instance, the walls with the through-hole interconnect 224 in the wall 336 are first formed and then scintillator material (e.g., a powder, a solid, etc.) is disposed in the open areas between the pixel walls. The electrically conductive material in the wall 336 may further reduce cross-talk between scintillator pixels. The wall 336 also includes non-electrically conductive material (e.g., non-electrically conductive nanomaterials, quantum dots, etc.) outside of the through-hole interconnect 224. Example wall thicknesses are less than 200 microns, including, but not limited to 160 microns, 100 microns, and 30 nanometers.

In a variation, the wall 336 (and/or other walls of the second scintillator layer 206) includes a conductive anti-scatter material. In one instance, the wall 336 (and/or other walls of the second scintillator layer 206) is the through-hole interconnect 224 and the corners are insulated. In another instance, the through-hole interconnect 224 is insulated in the wall 336 (and/or other walls of the second scintillator layer 206), and the corners may or may not be insulated.

The exploded view also shows a perspective view from a top 346 of the second photosensor layer 208. A top contact 348 is located at a top surface 350 of a photosensor pixel 352 of the second photosensor layer 208. A bottom contact 354 (not visible in this view, but visible at in the view at 360) is located at a bottom 356 of the photosensor pixel 352. An interconnect 358 extends from the top contact 348 to the bottom contact 356. The bottom contact 338 of the second scintillator layer 206 and the top contact 348 of the second photosensor layer 208 are in physical and electrical contact is the assembled structure. At 360, a perspective view from the bottom 356 shows the interconnect 358, the bottom contact 354 at an edge 362 of the second photosensor layer 208, and a bottom electrode 364 for the second photosensor layer 208.

The processing electronics 210 (FIG. 2) includes electrical contacts for both the bottom contact 354 of the second photosensor layer 208 for routing the signal from the photosensor pixel 306 of the first photosensor layer 204, and the bottom contact 364 of the second photosensor layer 208 for routing a signal from the photosensor pixel 352 of the second photosensor layer 208. FIG. 2 shows the processing electronics 210 as a single layer. However, it is to be appreciated that the processing electronics 210 may be a single ASIC, include an ASIC for each of the photosensor layers 204 and 208, etc. Where it includes an ASIC for each of the photosensor layers, signals from the bottom contact 354 are routed to one ASIC and signals from the bottom contact 364 are routed to the other ASIC.

Figure 5:
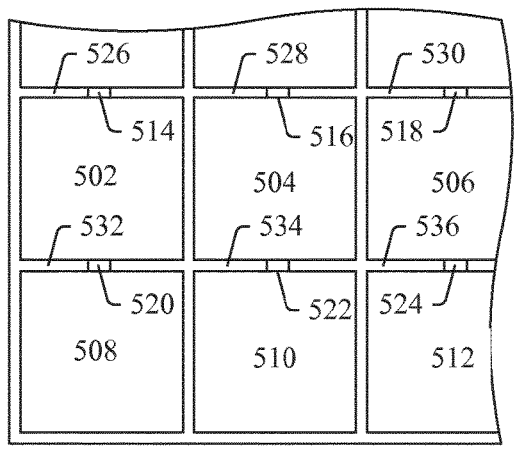
FIGS. 5-10 diagrammatically illustrate variations in the location of the integral through-hole interconnect in the scintillator layer.
Figure 6:
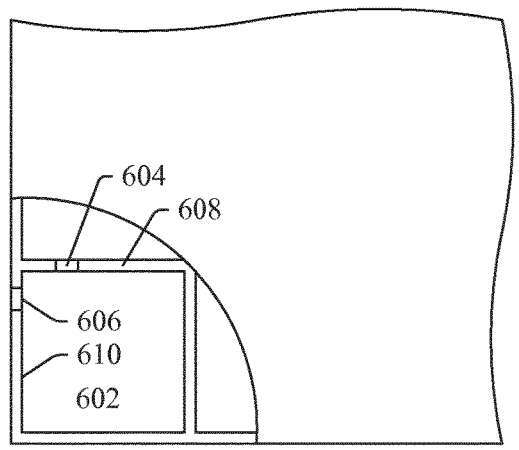
Figure 7:
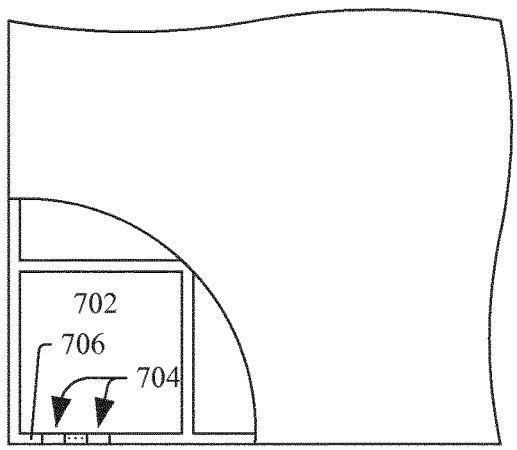
Figure 8:
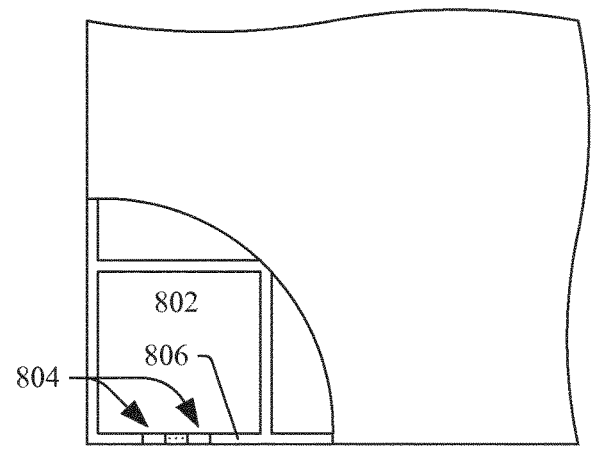
Figure 9:
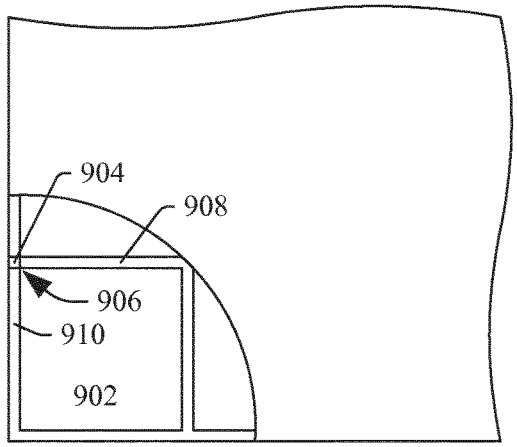
Figure 10:
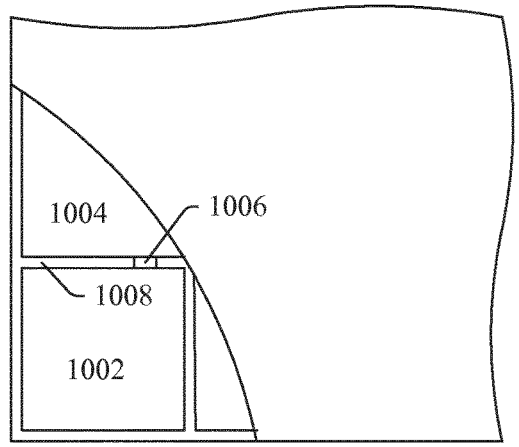

FIGS. 5-10 show variations of the routing of the through-hole interconnect 224. In FIG. 5, each scintillator pixel 502, 504, 506, 508, 510 and 512 has an associated through-hole interconnect 514, 516, 518, 520, 522 and 524 in an adjacent wall 526, 528, 530, 532, 534 and 536 for routing signals from a corresponding pixel of the upper photosensor layer 204 above it. In FIG. 6, a single scintillator pixel 602 has multiple through-hole interconnects 604 and 606, each disposed in a different wall 608 and 610. In FIG. 7, a single scintillator pixel 702 has multiple through-hole interconnects 704 disposed asymmetrically about a single wall 706. In FIG. 8, a single scintillator pixel 802 has multiple through-hole interconnects 804 disposed symmetrically about a single wall 806. In FIG. 9, a single scintillator pixel 902 has a through-hole interconnect 904 disposed at a corner 906 between walls 908 and 910 where the walls 908 and 910 intersect. In FIG. 10, two neighboring scintillator pixels 1002 and 1004 share a single through-hole interconnect 1006 disposed in a wall 1008 between the two scintillator pixels 1002 and 1004. Other variations are also contemplated herein.

Figure 11:
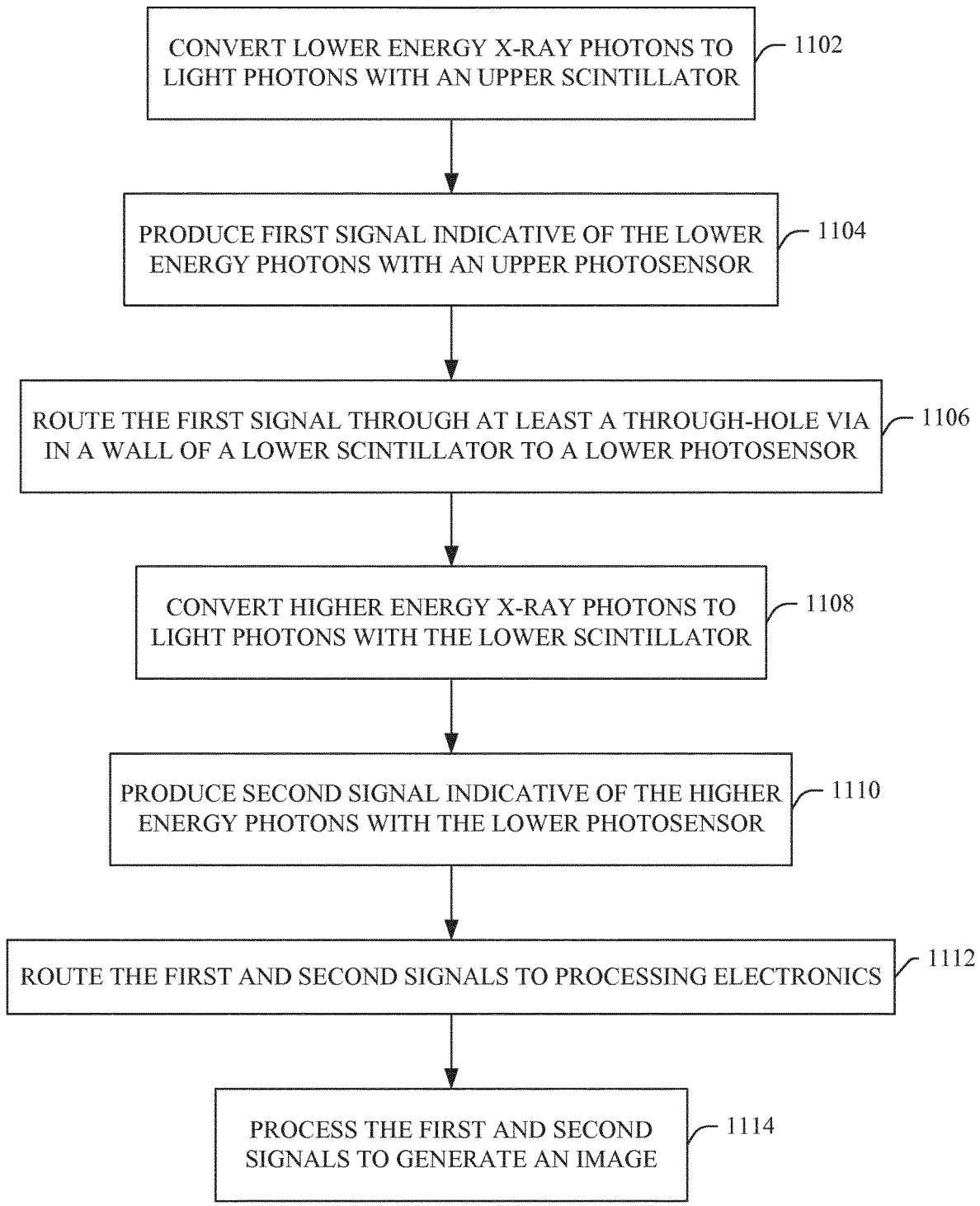
FIG. 11 illustrates an example method in accordance with an embodiment herein.

FIG. 11 illustrates an example method in accordance with the embodiment described herein.

At 1102, the upper scintillator layer 202 absorbs lower energy X-ray photons and converts them to first light photons.

At 1104, the upper photosensor 204 receives the first light photons and produces a first electrical signal indicative thereof.

At 1106, the first electrical signal is routed through the through-hole interconnect 224 integral in the wall 336 of the lower scintillator layer 206 and through the interconnect 358 of the lower photosensor 208 to the processing electronics 210.

At 1108, the lower scintillator layer 206 absorbs higher energy X-ray photons and converts them to second light photons.

At 1110, the lower photosensor 208 receives the second light photons and produces a second electrical signal indicative thereof.

At 1112, the second electrical signal is routed from the electrode 360 of the lower photosensor 208 to the processing electronics 210.

At 1114, the first and second signals are processed to generate image data.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A scintillator layer for a radiation detector tile, comprising:
a plurality of scintillator pixels;
walls of non-scintillation material and light reflective material surrounding each pixel of the plurality of scintillator pixels, wherein the walls form a single continuous wall; and
at least one electrically conductive interconnect for a pixel, wherein the at least one electrically conductive interconnect extends within the wall of the pixel along an entire depth of the wall, and wherein the at least one electrically conductive interconnect includes at least one of electrically conductive nanomaterials and electrically conductive anti-scatter material.

2. The scintillator layer of claim 1, further comprising:
at least a second electrically conductive interconnect for the scintillator pixel, wherein the at least second electrically conductive interconnect is disposed in the wall of the scintillator pixel.

3. The scintillator layer of claim 1, further comprising at least a second electrically conductive interconnect for the scintillator pixel, wherein the at least second electrically conductive interconnect is disposed in a second different wall of the scintillator pixel.

4. The scintillator layer of claim 1, wherein the at least a one electrically conductive interconnect is disposed in a corner of the scintillator pixel.

5. The scintillator layer of claim 1, wherein the wall is an outer wall of the scintillator layer.

6. The scintillator layer of claim 1, wherein the wall is an inner wall of the scintillator layer.

7. A multi-energy detector array, comprising:
a detector tile, including:
an upper scintillator layer;
an upper photosensor optically coupled to the upper scintillator layer;
a lower scintillator layer electrically coupled to the upper photosensor and including at least one scintillator pixel surrounded by at least one wall of non-scintillation material; and
a lower photodetector optically and electrically coupled to the lower scintillator layer; and
wherein the at least one wall includes at least one electrically conductive interconnect that extends from a top edge of the wall at the upper photosensor to a bottom edge of the wall at the lower photodetector.

8. The detector array of claim 7, wherein the at least one electrically conductive interconnect comprises an electrically conductive metal.

9. The detector array of claim 7, wherein the at least one electrically conductive interconnect comprises electrically conductive nanomaterials.

10. The detector array of claim 7, wherein the upper photosensor includes an electrical readout contact in electrical contact with the at least one electrically conductive interconnect.

11. The detector array of claim 10, wherein the electrical readout contact is located at an edge of a photosensor pixel, and the upper photosensor includes a readout electrode disposed at a central region of a photosensor pixel and an electrically conductive trace electrically connecting the readout electrode and the electrical readout contact.

12. The detector array of claim 7, wherein the lower photodetector includes:
a top electrical contact at an upper edge of a photosensor pixel and is electrical contact with the at least one electrically conductive interconnect of the lower scintillator layer;
a bottom electrical contact at a lower edge of the photosensor pixel;
an electrical interconnect electrically connecting the top electrical contact and the bottom electrical contact; and
a readout electrode at a central region of the photosensor pixel.

13. The detector array of claim 7, further comprising:
processing electronics electrically coupled to the lower photodetector.

14. The detector array of claim 13, wherein the processing electronics comprises at least one application specific integrated circuit which is in electrical communication with the bottom electrical contact of the lower photodetector and the readout electrode of the lower photodetector.

15. The detector array of claim 7, wherein the lower scintillator layer includes:
a plurality of scintillator pixels;
a plurality of through-hole interconnects, including one for each of the plurality of pixels; and
a plurality of walls between the plurality of scintillator pixels, wherein each of the plurality of through-hole interconnects is located in a different wall of the plurality of walls.

16. The detector array of claim 7, wherein the lower scintillator layer includes:
at least two through-hole interconnects for a same scintillator pixel, and each of the at least two through-hole interconnects is located in a different wall of the pixel.

17. The detector array of claim 7, wherein the lower scintillator layer includes:
a plurality of through-hole interconnects for a same scintillator pixel, and each the plurality of through-hole interconnects are located in a same wall of the pixel.

18. The detector array of claim 7, wherein the through-hole interconnect is located at a corner between two walls of the pixel.

19. The detector array of claim 7, wherein the lower scintillator layer includes at least two neighboring scintillator pixels with a shared wall therebetween, and the through-hole interconnect is disposed in the shared wall.

20. The detector array of claim 19, wherein readout contacts of both of the at least two neighboring scintillator pixels are in electrical communication with the through-hole interconnect in the shared wall.

21. A method for routing photosensor signals in a stacked multi-energy detector tile including at least an upper scintillator layer, an upper photosensor optically coupled to the upper scintillator layer, a lower scintillator layer electrically coupled to the upper photosensor, and a lower photodetector optically and electrically coupled to the lower scintillator layer, the method comprising:
receiving, at the upper scintillator layer, X-ray photons including first energy X-ray photons and second energy X-ray photons, wherein the first energy is less than the second energy;
converting, with the upper scintillator layer, the first energy X-ray photons to first light photons;
detecting, with the upper photosensor, the first light photons and producing a first electrical signal indicative thereof;
routing, through a through-hole interconnects in a side wall of the lower scintillator layer, the first electrical signal to the lower photodetector; and routing, with the lower photodetector, the first electrical signal to processing electronics.

22. The method of claim 21, further comprising:
receiving, at the lower scintillator layer, the second energy X-ray photons;
converting, with the lower scintillator layer, the second energy X-ray photons to second light photons;
detecting, with the lower photosensor, the second light photons and producing a second electrical signal indicative thereof;
routing, with the lower photodetector, the second electrical signal to the processing electronics.

23. The method of claim 21, further comprising:
routing the second electrical signal from a central region of a pixel of the lower photodetector to an edge of the pixel, prior to routing the first electrical signal to the lower photodetector through the through-hole interconnects in the side wall of the lower scintillator layer.

24. The method of claim 23, further comprising:
routing the first electrical signal from the central region to the edge of the pixel with an electrically conductive trace disposed on a bottom of the pixel.

25. The method of claim 23, further comprising:
routing the first electrical signal to the edge of the pixel within the pixel.

* * * * *